United States Patent [19]

Keller

[11] 4,246,060
[45] Jan. 20, 1981

[54] PLASMA DEVELOPMENT PROCESS CONTROLLER

[75] Inventor: Jed V. Keller, Mesa, Ariz.
[73] Assignee: Motorola, Inc., Schaumburg, Ill.
[21] Appl. No.: 472
[22] Filed: Jan. 2, 1979
[51] Int. Cl.³ .................. G01N 21/00; B44C 1/22; C03C 15/00; C03C 25/06
[52] U.S. Cl. .................. 156/345; 156/627; 156/643; 156/646; 204/192 E; 356/341
[58] Field of Search .............. 156/345, 626, 627, 643, 156/646; 250/531; 355/3 DD; 204/164, 192 E, 298; 356/311, 314, 338, 316, 341, 436, 437, 226; 430/323, 434

[56] References Cited
PUBLICATIONS

Kodak Microelectronics Seminar, 1976, A Study of the Optical Emission From A RF Plasma During Semiconductor Etching, by Harshbarger et al., pp. 1–24.

Primary Examiner—William A. Powell
Attorney, Agent, or Firm—Paul F. Wille

[57] ABSTRACT

End point detection in developing photoresist is accomplished by monitoring the output of a photodetector and sensing a plateau in the output.

6 Claims, 2 Drawing Figures

4,246,060

PLASMA DEVELOPMENT PROCESS CONTROLLER

BACKGROUND OF THE INVENTION

This invention relates to semiconductor fabrication and, in particular, to apparatus for plasma etching coatings on a semiconductor substrate.

During approximately the past decade, plasma etching has received continuously increasing attention as an alternative to wet chemical etching, due to both superior process control as well as environmental considerations. As known by those of skill in the art, plasma etching is largely a chemical process in which an essentially neutral cloud of gas is ionized by RF (radio frequency) energy. The radicals produced in the plasma are chosen to react with the particular material to be etched. For example, carbon tetrafluoride ($CF_4$) reacts with silicon to produce silicon tetrafluoride ($SiF_4$), which is a gas at room temperature and can thus be removed by exhausting the chamber containing the silicon wafers.

The plasma etching processes to date have been controlled by a timer. The optimum time is previously determined empirically and depends, as known in the art, on temperature, gas pressure, flow rate, and RF power. It is thus apparent that, even with time preset, the process requires careful control.

It has also been found in the prior art that the luminosity of the plasma changes when the etch cycle is complete. This, however, has only been used as a supplementary system check to assure that the etching has been permitted to continue for an adequate length of time, for "ashing" or complete removal of the photoresist.

In copending patent application Ser. No. 939,586, originally filed June 17, 1976 and assigned to the assignee of the present invention, there is disclosed a plasma developable photoresist exhibiting different etch rates for the exposed and unexposed portions of the photoresist. As with other plasma etch systems, time and other process parameters must be accurately controlled to fully develop the photoresist without removing it entirely. While the different etch rates are beneficial and permit reproducible results, greater accuracy or flexibility, or both, in the process is always desired.

SUMMARY OF THE INVENTION

In view of the foregoing, it is therefore an object of the present invention to control plasma development in accordance with the luminosity of the plasma.

Another object of the present invention is to provide an improved method for the plasma development of photoresist.

A further object of the present invention is to provide apparatus for detecting the completion of the development of a photoresist by a plasma.

Another object of the present invention is to permit greater flexibility in process parameters by providing an adaptive control of plasma development.

The foregoing objects are achieved in the present invention wherein a photodetector is used to monitor the luminosity of the plasma. It has been found that during plasma development of photoresist, the generally decreasing luminosity of the plasma remains relatively constant for a brief period after the photoresist is fully developed. Terminating the plasma discharge at this point yields a fully developed, i.e. patterned, photoresist without substantial removel of photoresist from areas in which it was intended it remain.

BRIEF DESCRIPTION OF THE DRAWINGS

A more complete understanding of the present invention can be obtained by considering the following detailed description in conjunction with the accompanying drawings, in which.

DETAILED DESCRIPTION

As known in quantum mechanics, atoms seek the lowest energy state as a stable configuration. The applied RF energy used to generate a plasma not only dissociates atoms in a molecule to create ions but also excites the electrons of the atoms or molecules to higher energy levels. When the atoms revert to a lower energy level, energy can be released in the form of a photon. If the difference in energy levels is the right amount of energy, the photon emitted is in the infra-red and visible portions of the electromagnetic frequency spectrum. These portions are detectable by a silicon photocell.

It is believed that in accordance with the present invention, what is being monitored is the emission from etch products as they are removed from the substrate as a gas. In a particular example where organic photoresist is used, it is believed that emission from the carbon monoxide (CO) radical is being monitored. In this case, radiation (light) from other atoms or radicals in the plasma is, in effect, noise. As more fully explained hereinafter, it has been found that the desired radiation can be made to exceed the background radiation or noise.

Figure 1:
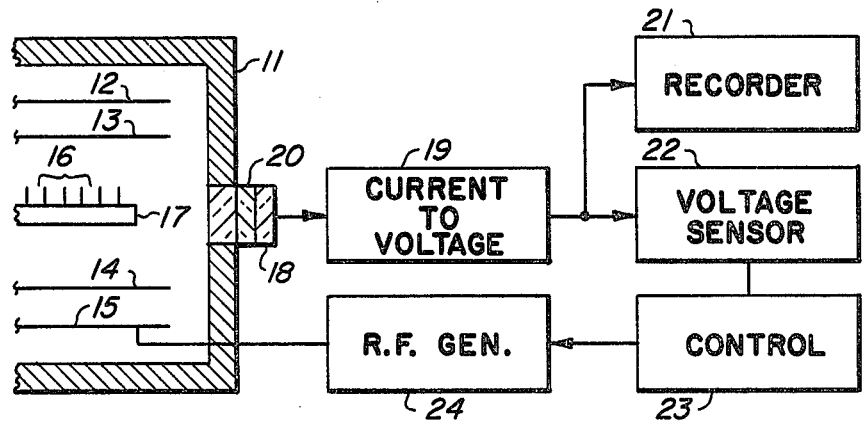
FIG. 1 is a preferred embodiment of a control system in accordance with the present invention.

FIG. 1 illustrates a preferred embodiment of the present invention in which a closed loop feedback system is used to control the duration of the plasma etch. Specifically, a suitable plasma processing chamber 11 contains a plurality of electrodes 12–15 for generating and sustaining a plasma in the gas contained therein. The plasma envelopes and etches the photoresist on the surface of wafers 16, which are contained in a suitable carrier 17. Exposed to the light produced by the plasma discharge is photocell 18 which may for example be optically coupled to the plasma by way of a quartz window. The output of photocell 18 is converted to a voltage by current-to-voltage converting circuit 19, which is well known per se in the art. The output voltage from converter 19 is coupled to recorder 21 and voltage sensor 22. Recorder 21 may be utilized to simply keep a record of the processing of particular wafers or, if in the form of a strip chart recorder, may be visually inspected for manual control of the process.

Figure 2:
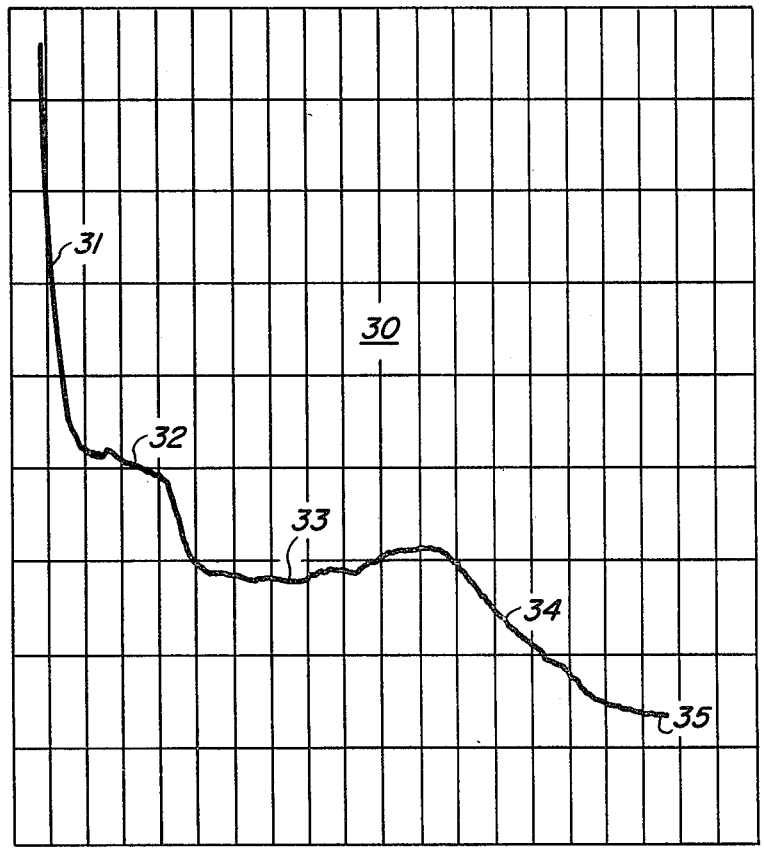
FIG. 2 is a chart illustrating the luminosity vs. time characteristic of the plasma.

The output of converter 19 is illustrated in FIG. 2 as curve 30 having several portions indicative of various stages of etching. Specifically, portion 31 is simply a characteristic of the particular chamber and photo detector utilized and is caused by a relatively bright output when the plasma is initially turned on, believed due to outgassing of impurities within the chamber. Portion 32 indicates a generally declining luminosity of the plasma indicative of the initital etching of the photoresist during which time the more easily etched portions of the resist are chemically removed by the plasma, leaving the desired pattern.

After a length of time depending upon a variety of process parameters, the luminosity of the discharge plateaus as indicated by portion 33. This plateau in the curve indicates that the pattern is completely formed and that the plasma is starting to etch the remainder of the photoresist. As the plasma proceeds to etch the remainder of the photoresist the luminosity of the plasma discharge declines as indicated by portion 34. When the plasma etch is completed the luminosity of the discharge is at its lowest value as indicated by portion 35 of curve 30.

In repeated processing of wafers, it has been found that curves similar to curve 30 are produced by the photo detector, comprising photo cell 18 and converter 19, and that these curves provide detailed information on the status of the plasma etch. Termination of the plasma etch during the plateau portion 33 of curve 30 reveals fully developed photoresist, i.e., the pattern is completely formed, with substantial amounts of photoresist remaining to protect the desired portions of the wafer.

Referring again to FIG. 1, in accordance with the present invention the plasma development process is adaptively controlled by monitoring the output of converter 19 and detecting plateau 33. When the voltage corresponding to plateau 33 is detected, a signal is sent to control circuitry 23 which in turn terminates the plasma by shutting off RF generator 24. Control circuit 23 may comprise any suitable shut off or turn down controls, known per se in the art, for terminating the RF energy from generator 24.

Voltage sensor 22 may comprise any of a variety of electronic circuits known per se in the art. For example, voltage sensor 22 may simply comprise a comparator having as one input thereto the output voltage from converter 19. The other voltage is a preset voltage corresponding to the voltage of plateau 33. Alternatively, voltage sensor 22 may comprise analog processing circuitry for detecting the rate of change of the output voltage from converter 19. Such circuitry may for example comprise a differentiating amplifier coupled to threshold sensing circuitry or may comprise suitable sample and hold circuitry which samples the output of converter 19 and compares the current sample to the preceding sample, putting out a signal to control 23 when the difference between successive samples is within a predetermined range. These circuits for detecting plateau 33 are all well known per se in the art.

There is thus provided by the present invention an improved control system for plasma development of photoresists in which the duration of the development is adaptively controlled in accordance with the luminosity of the plasma. Thus, processing wafers in accordance with the present invention enables one to tolerate greater variations in the other process parameters.

Having thus described the invention it will be apparent to those of ordinary skill in the art that various modifications can be made within the spirit and scope of the present invention. For example, photocell 18 may simply comprise a broadband silicon photodiode the response of which extends from the infra-red through the visible portions of the radiant energy spectrum. In this situation, the photocell responds to the emission from residual nitrogen in the plasma chamber, producing peak 31, which declines as the nitrogen is removed. Such residual gases may cause background noise, the spectrums of which may be filtered to enhance the response of photocell 18 to the desired portion of the spectrum. This is accomplished by inserting a filter, such as filter 20 in FIG. 1, between the photocell and the window of the etching chamber. These filters may have any desired color or bandwidth, depending upon the portion of the spectrum it is desired to monitor.

What is claimed is:

1. In apparatus for plasma etching having an evacuable chamber, for containing a gas etchant and the material to be etched, and a source of radio frequency energy coupled to the interior of said chamber for sustaining a plasma, the improvement comprising:
    photodetector means optically coupled to the interior of said chamber for producing a variable level output signal representative of the luminosity of said plasma; and
    means for detecting a temporary uniformity in the level of said output signal as indicative of the end of a first phase of said plasma etch.

2. The apparatus as set forth in claim 1 wherein said detecting means detects a predetermined level in said output signal.

3. The apparatus as set forth in claim 1 and further comprising means for recording the output of said photodetector means.

4. The apparatus as set forth in claim 1 and further comprising control means connected to said level detecting means and to said source of radio frequency energy for turning off said source when said uniformity is detected.

5. The apparatus of claim 1 wherein said photodetector means comprises a photocell and a current to voltage converter.

6. The apparatus as set forth in claim 5 wherein said photodetector means further comprises spectral filter means interposed between said photocell and said plasma.

* * * * *